United States Patent [19]

Fürst et al.

[11] Patent Number: 4,532,023

[45] Date of Patent: Jul. 30, 1985

[54] ELECTROCHEMICAL GAS ANALYZER FOR DETERMINATION OF SULPHUR DIOXIDE CONTENT OF GASES

[75] Inventors: Leander Fürst; Jiri Divisek, both of Julich, Fed. Rep. of Germany

[73] Assignee: Kernforschungsanlage Julich GmbH, Fed. Rep. of Germany

[21] Appl. No.: 585,431

[22] Filed: Mar. 2, 1984

[30] Foreign Application Priority Data

Mar. 12, 1983 [DE] Fed. Rep. of Germany ....... 3308888
Mar. 12, 1983 [DE] Fed. Rep. of Germany ... 8307201[U]

[51] Int. Cl.$^3$ ............................................. G01N 27/50
[52] U.S. Cl. ..................... 204/402; 204/409; 204/431
[58] Field of Search ............... 204/402, 409, 411, 412, 204/431, 1 F

[56] References Cited

U.S. PATENT DOCUMENTS 4,409,069 10/1983 Luft ..................................... 204/1 T Primary Examiner—G. L. Kaplan
Attorney, Agent, or Firm—Omri M. Behr

[57] ABSTRACT

The invention is concerned with an electrochemical gas analyzer for determining the sulphur dioxide content of certain gases in particular, flue gases. The device comprises a measuring cell containing a measuring electrode for the determination of the depolarization current and further comprising an unpolarizable electrode in the same electrolyte. The gas input flow is utilized to cause a circulation of electrolyte containing the dissolved gas which moves in the space between the measuring and counter-electrode. The electrolyte is continuously renewed and the electrolyte leaving the cell is regeneratd and recycled. The sulphur dioxide dissolved in the electrolyte is removed outside the cell by treatment with air in the presence of activated charcoal.

3 Claims, 7 Drawing Figures

ELECTROCHEMICAL GAS ANALYZER FOR DETERMINATION OF SULPHUR DIOXIDE CONTENT OF GASES

BACKGROUND OF THE INVENTION

The invention is concerned with an electrochemical gas analyzer for determining the sulphur dioxide content of certain gases, in particular, flue gases. The device comprises a measuring cell containing a measuring electrode for the determination of the depolarization current and further comprising an unpolarizable electrode in the same electrolyte. The gas input flow is utilized to cause a circulation of electrolyte containing the dissolved gas which moves in the space between the measuring and counter-electrode. The electrolyte is kept in circulation and constantly renewed. The sulphur dioxide dissolved in the electrolyte is removed outside the cell by treatment with air in the presence of activated charcoal.

The control of sulphur dioxide content in flue and other exhaust gases is a particularly important task in the field of measurement technology. All of the previously known available measuring devices which are based on different principles (such as infrared, conductivity, UV, etc.) are either very expensive or can only be used in limited environments.

There has previously been developed an electrochemical gas analyzer utilizing the foregoing general principles which is disclosed in U.S. Pat. No. 4,409,069. This device is very economical and may be utilized over a substantial range of concentrations. In this analyzer electrolyte is added dropwise to the measuring cell and the used electrolyte removed therefrom. Similarly, the sulphur dioxide is removed from the electrolyte by treatment with air in the presence of activated charcoal outside the cell and recirculated to the cell. Dilute copper sulfate may be utilized therein as the electrolyte.

Since the measuring effect is dependent upon the sulphur dioxide concentration in the electrolyte which increases cumulatively with contact time up to the achievement of the equilibrium value, it is clear that the sensitivity of such a device rises with the increase in saturation time of the electrolyte. For this reason, the change in electrolyte content of the cell has heretofore been provided to be of the order of 0.01 to 0.1 of the total volume per minute (see for example, DE-AS No. 1091776). Such an electrolyte exchange rate is so small that considerations relating to collection, regeneration, and recycling need not usually cause concern and must be dealt with only when substantial concentrations of copper salts are in the electrolyte. Under these circumstances the required removal of sulphur dioxide by oxidation with oxygen in the presence of activated charcoal is achieved by suspension of activated charcoal in electrolyte and the passage of air thru such a suspension.

In practice however, it has been found that the stability and reproduceability of the measurement results and also its only approximate linear relationship to the $SO_2$ content over a wide measuring range leaves something to be desired. The suggestion has been made in the aforementioned DE-AS that this problem could be solved by efficient temperature control. Regrettably, even the use of a second cell utilized as a reference cell carrying sulphur dioxide free carrier gas as previously conceived by the Applicants, does not obviate the problem.

SUMMARY OF THE INVENTION

Surprisingly, it has been found that while a substantially higher exchange of electrolyte in the measuring cell leads to a certain reduction in the level of utilizable measuring signals it also leads to a substantial improvement in the mode of operation of the cell, in that an improvement in the linear relationship between the measuring value for the $SO_2$ content as well as the signal stability is obtained, and thus, the response time of the system is improved. Thus, it is advantageous to provide for a rate of electrolyte exchange in the cell which is at least 50% of the electrolyte volume of the cell per minute. Since, in increasing electrolyte exchange, the signal strength diminishes, the maximum level of electrolyte exchange should also be taken into consideration. It should also be borne in mind that a vigorous electrolyte exchange also requires its regeneration and recycling.

The apparatus of the present invention (the analyzing device) comprises an electrolyte inflow control means in the circuit at the entry to the cell for the replacement of electrolyte therein, which operates at approximately 0.5 to 5 times the volume of cell per minute. The apparatus further comprises, at a location proximate to the electrolyte outflow from the cell, an activated charcoal cartridge for the removal of sulphur dioxide, provided with air ingress means. Wherein the size and rate of electrolyte provision and removal is such that the charcoal is at least partially only wetted by the electrolyte flowing out of the cell. That means, the activated charcoal should be wetted by liquid films and not flooded by the electrolyte, at least in a part of the cartridge. The relationship of the gas thruput to the electrolyte thruput should be of the order of 10 to 40:1 (v/v).

The oxidation cartridge containing the activated charcoal which serves to remove the sulphur dioxide is constructed to have a substantially greater cross-section than the measuring cell. Thus, a rather large surface area is provided to enable the charcoal, the electrolyte and the oxygen to come and remain in contact with each other. This purpose is achieved in that there is provided a substantially vertically oriented cartridge having an electrolyte outflow means at the lower end thereof comprising approximately 50 to 100 ml. of coarse grain activated charcoal, having a grain size of at least 1 mm. to the upper surface of which the electrolyte is provided. The upper end of the cartridge is also provided with an air access means.

Preferably, the measuring electrode is a carbon electrode most suitably in the form of a graphite rod, while the counter-electrode is made of copper. If desired, the two electrodes may be separated by a diaphragm confining the electrolyte flow stream between diaphragm and anode.

For production reasons, it is particularly desirable to construct the cell portion of the device out of a block into which there is provided a substantially vertical bore to contain the cell unit itself. A second bore whose lower end connects to the aforesaid cell bore is placed in the block with its axis at an acute angle with respect to the axis of cell bore. A third bore connects the upper portions of the aforesaid two bores running downwardly at a small angle acute from the horizontal. The second bore serves as the gas inlet source. The third, moderately downwardly directed connecting bore serves as a gas and electrolyte outflow means and, in the mode illustrated herein, because of its relative length, also serves as a settling segment. The electrolyte inflow means opens into this bore between the first two bores, suitably by means of an outflow capilliary whose upper end is located in a reservoir of predetermined electrolyte level.

In the recycling circuit of the electrolyte, there is suitably provided a large storage vessel for regenerated electrolyte (a volume of approximately 5 liters has been found suitable) whose level is controlled by a further level controlled water input device. In this manner, evaporation losses are compensated and the concentration of electrolyte is kept substantially constant. This supply vessel is suitably maintained at a level below that of the cell so that the electrolyte flowing from the cell after the passage thereof through the sulphur dioxide removing means and thru the mechanical filter means desirably located thereafter in the circuit (for example, a paper or fabric filter or a glass sinter) will readily run into the storage vessel. A pump means is attached to this vessel which can move the electrolyte, now free of sulphur dioxide, from the storage means into the electrolyte supply control means (which is suitably formed by a constant level vessel equipped with an outflow capillary in order to compensate for variations in the pump delivery).

It is further desirable, as has been previously shown in U.S. Pat. No. 4,409,069, to provide a twin cell (also containing a branch tube for the provision of gases to achieve the circulation of electrolyte) wherein both cells are provided, suitably as borings, in a single block). Thus, the second cell can serve as a reference cell thru which ordinary air is passed, thus providing the measuring value by determining the difference in current between the two cells. This mode of operation obviates the otherwise present requirement for thermal stabilization which would be necessary in the case of the determination of sulphur dioxide content in flue gases in which different temperature ranges could well be present.

The test gases suitably flue gases, are provided into the electrolyte circuit in the predetermined ratio by means of a probe and a gas forwarding pump located proximate to the flue itself and thus passed into the measuring cell. Where the automatic control of the gas input is desired, a manostat device, may be provided as mentioned in the above-referenced U.S. Patent. Suitably however, hot gases are routed through a pressure control means which basically comprises a flow-thru chamber provided with a barrier wall in the form of a spring biased non-corrodable membrane operating upon one arm of a twin arm lever whose other arm acts as a capping device for the gas inflow means. It has been found desirable to be able to control the spring compression by means of a setting screw. Since substantially elevated temperatures, that is to say on the order of 100°-200° C. may be expected in the monitoring of flue gases, this membrane should be constructed of silicone rubber or fabric strengthened polytetrafluorethylene.

BRIEF DESCRIPTION OF THE DRAWINGS

The invention may be illustrated by the accompanying schematic drawings.

FIG. 1 shows the arrangement of a double cell device 1 with measuring cell 2 and reference cell 3 whose used electrolyte flows over a common path 4 to an $SO_2$ filter 5 from which after mechanical filtering at 6 the electrolyte, freed of sulphur dioxide and gross contaminants runs into level controlled storage means 7.

Figure 1:
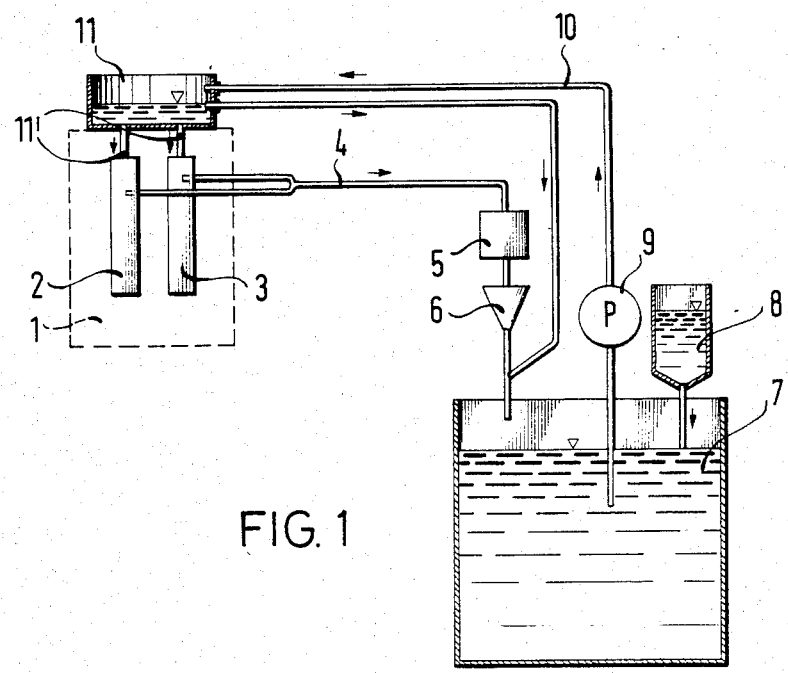
FIG. 1 shows an electrolyte circulation circuit for a sulphur dioxide analyzing means comprising a dual cell.

The level of this reservoir is maintained by means of a water addition arrangement 8 provided with a constant level control means. This compensates for the evaporation losses of fluid and maintains the concentration of electrolyte at a substantially constant level.

A pump 9 connects lead line 10 to a level control reservoir 11 equipped with flow thru capilliaries 11' whose lower ends exit into cells 2 and 3 (or the corresponding connection lines to the gas inflow serving branch tubes). Thus, the electrolyte is moved from reservoir 7 thru pump 9 via line 10 to storage means 11 and thus to the cells 2 and 3.

Figure 2:
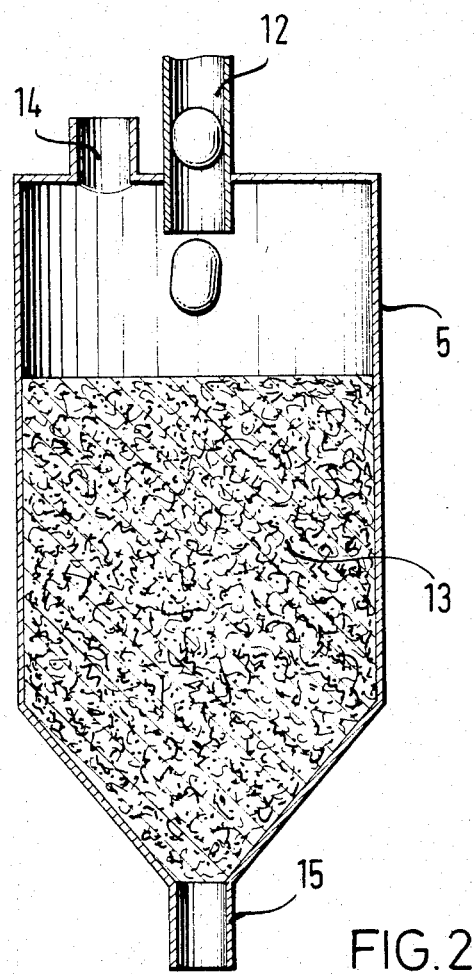
FIG. 2 is a cross sectional elevational view of the sulphur dioxide filter cartridge.

FIG. 2 shows the cross-section of the $SO_2$ filter comprising the activated charcoal bed 13 having inflow lead 12 and substantial air contact opening 14 and exit tube 15.

The $SO_2$ containing electrolyte enters thru tube 12 and the purified electrolyte having wetted charcoal bed 13 in the presence of air, exits thru 15.

Figure 3:
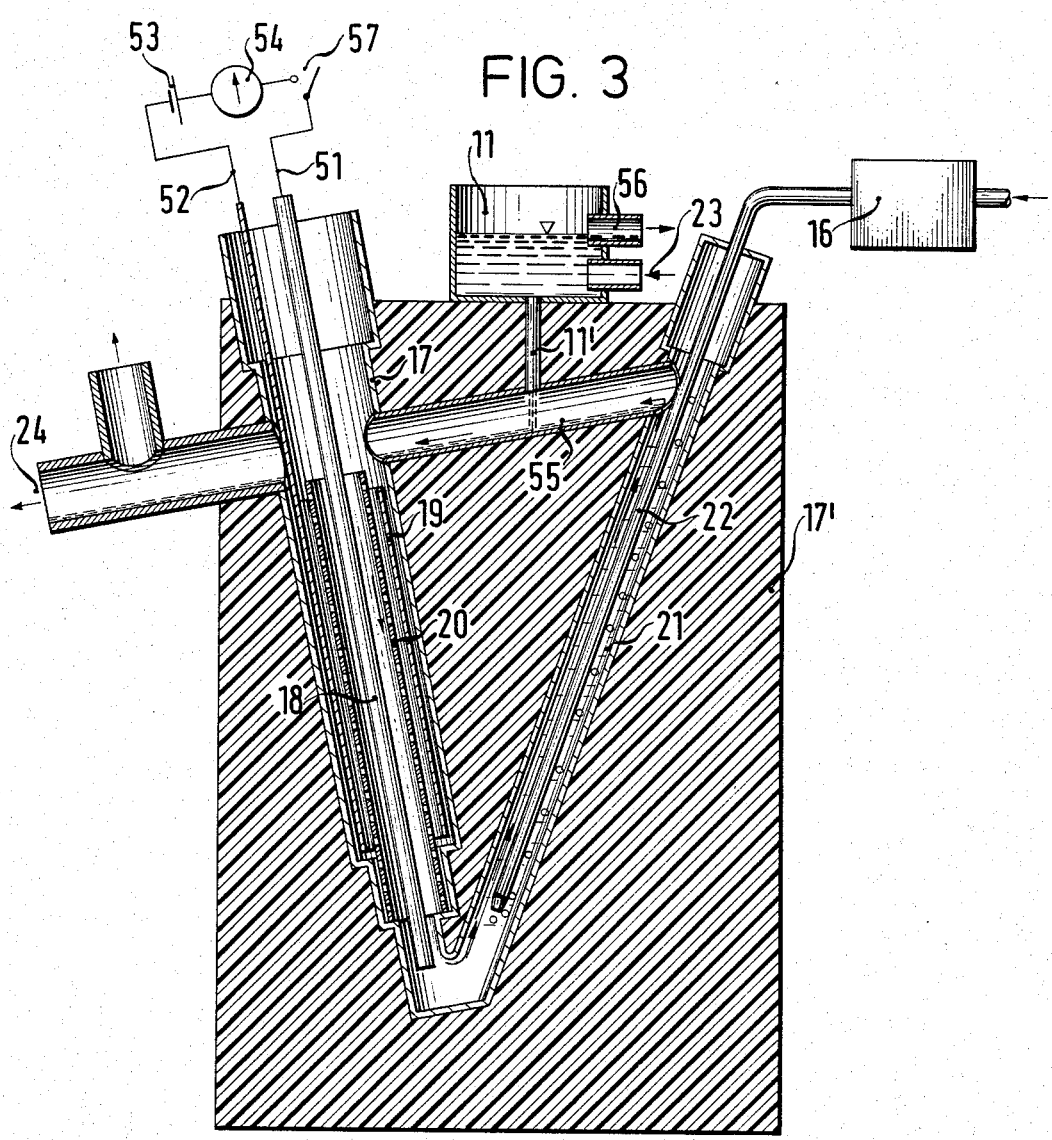
FIG. 3 is an elevational cross-sectional view of a single cell comprising the gas flow regulator in which the gas input means is controlled.

FIG. 3 shows the mode of construction and the utilization of a simple embodiment of measuring cell 2. A measuring electrode 18 in the form of a carbon rod is located in electrolysis cell 17 in block 17'. As counter electrode there is provided a copper tube 19 which is separated from the carbon rod 18 by means of a glass fritted cylinder 20. Communicating with the lower end of cell 17, is branch vessel 21 in the lower end of which is located the opening of tube 22. To the upper end of tube 22 is connected gas inflow control means 16.

Connecting bore 55 connects the upper ends of bores 21 and 17 to exit point 24. Storage means 11 comprises an inflow port 23, and a constant level outflow port 56. A capillary tube 11' runs from the bottom of 11 into connecting bore 55.

Electric leads 51 and 52 are connected to electrodes 18 and 19 respectively, between leads 51 and 52 are located potential source 53, current measuring means 54 and switch 57.

The electrolyte is pumped upwardly in bore 21 by the gas bubbled in thru 22, the circulation is added by inflow thru capilliary 11'. The circulatory action causes the electrolyte, loaded with gas, to flow between electrodes 18 and 19 so the current therebetween may be measured upon closure of switch 57, by measuring means 54.

Figure 4:
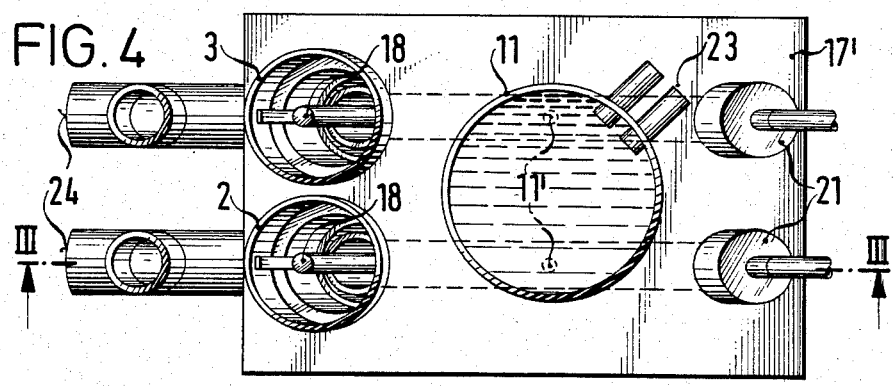
FIG. 4 is a plan cross-sectional view of a double cell device corresponding to the single cell device of FIG. 3.

FIG. 4 is a schematic plan view of the arrangement of FIG. 3 showing twin cells.

In the pumped electrolyte circuit from 24 to 23 in which the $SO_2$ is removed outside the cell, the slowly rising copper concentration changes have to be corrected after longer use. Since the concentration changes which occur in the monitoring of gases which only contain small amounts of sulphur dioxide, are low, and their influence on measuring value is insubstantial one can take care of this problem in the preferred embodiment by alternating the two cells between use as reference and measuring cells wherein the copper which is deposited in the measuring cell during oxidation is again dissolved by the oxygen contained in the air.

Figure 5:
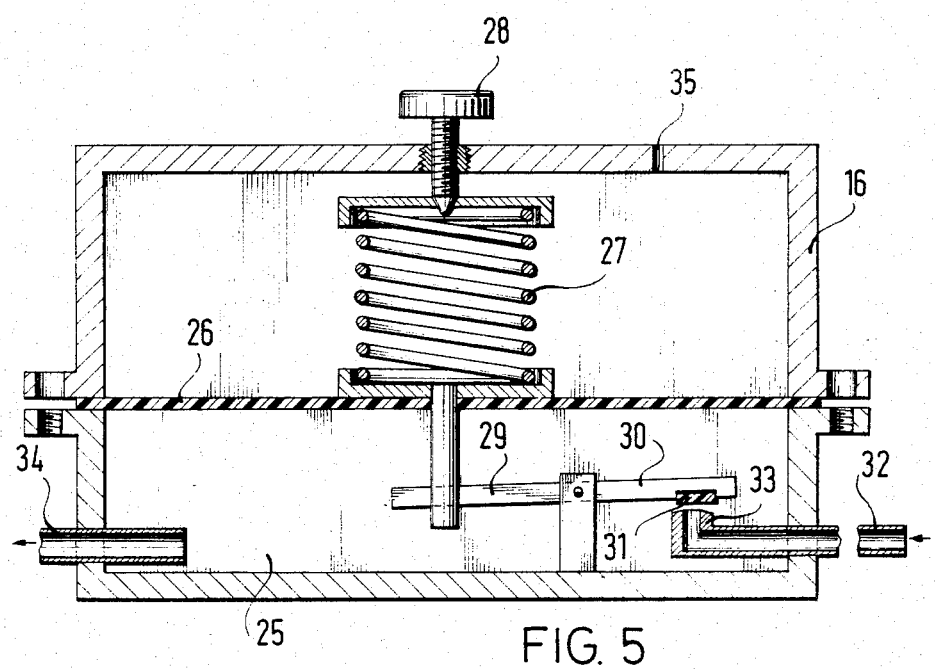
FIG. 5 is an elevational cross-sectional view of the pressure control device regulating the gas inflow.

FIG. 5 shows a pressure control device 16 comprising a flow-thru chamber 25 having a barrier means formed by membrane 26 out of a non-corrosable elastic material which is able to resist elevated temperatures, suitably silicone rubber or Teflon with fabric support. A spring 27 whose compression is controlled by control screw 28 biases membrane 26. The membrane is in operative connection via rod 47 with arm 29 of a two-armed lever whose other arm 30 comprises a closing element 31 which is interactable with the exit 33 of gas inlet line 32. Element 31 is suitably made of silicone rubber. Gas exit from the controlled is provided at 34, the controller further comprises a small opening 35 in the segment above the barrier wall. As the gas pressure in the lower chamber rises membrane 26 rises against the bias of spring 27. Opening 35 prevents pressure build up in the upper chamber. As membrane 26 moves upwardly rod 47 moves up lever 29 which causes pad 31 on lever 30 to partially close outlet 33. This causes a pressure drop, whereupon the control process will reverse.

Figure 6:
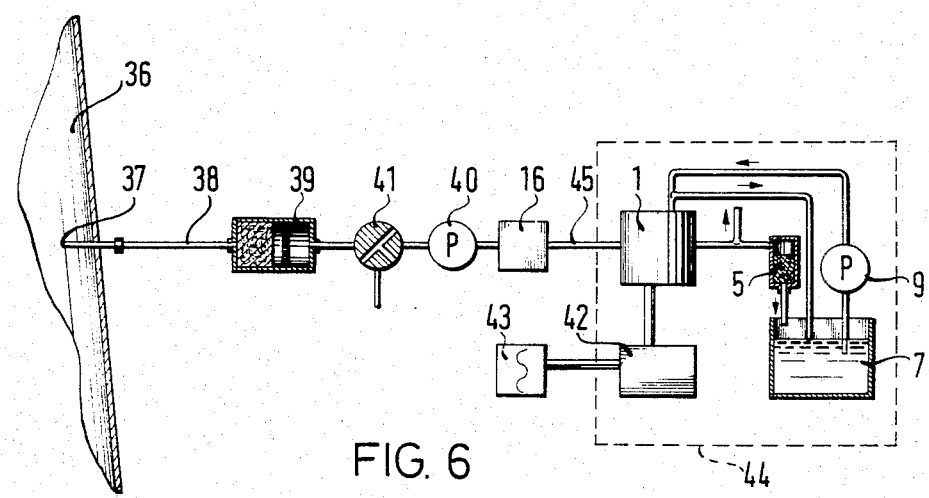
FIG. 6 is a schematic representation of the connection of analyzing means to a chimney showing the gas flow path.

FIG. 6 shows the mode of connection of a gas analyzing device of the present invention to a flue 36. The gas to be tested is taken via probe 37 through lead 38 to dust filter 39 by means of transfer pump 40. At point 41 measuring gas and calibration gas for example, pure gas, can be added as desired. The gas flows thru a pressure control means 16 (as shown in FIG. 5) to one unit of the double cell 1, 2 (as in FIG. 3) the other cell being supplied with $SO_2$-free air. In the cells the electrolyte is caused to circulate by gas inflow in the manner shown wherein the electrolyte coming from both cells passes thru $SO_2$ filter 5 into electrolyte storage means 7 from which fresh electrolyte is recycled to the double cell by means of electrolyte pump 9. At 42 the difference in the electric currents is noted and recorded by recording means 43. Phantom 44 indicates the actual portion of the housing of the analyzing means (those portions show the leftwards of the housing, namely part 16, 37 thru 41 and 45) are maintained at such a temperature that the condensation point of the test gases is always exceeded.

EXAMPLE

Figure 7:
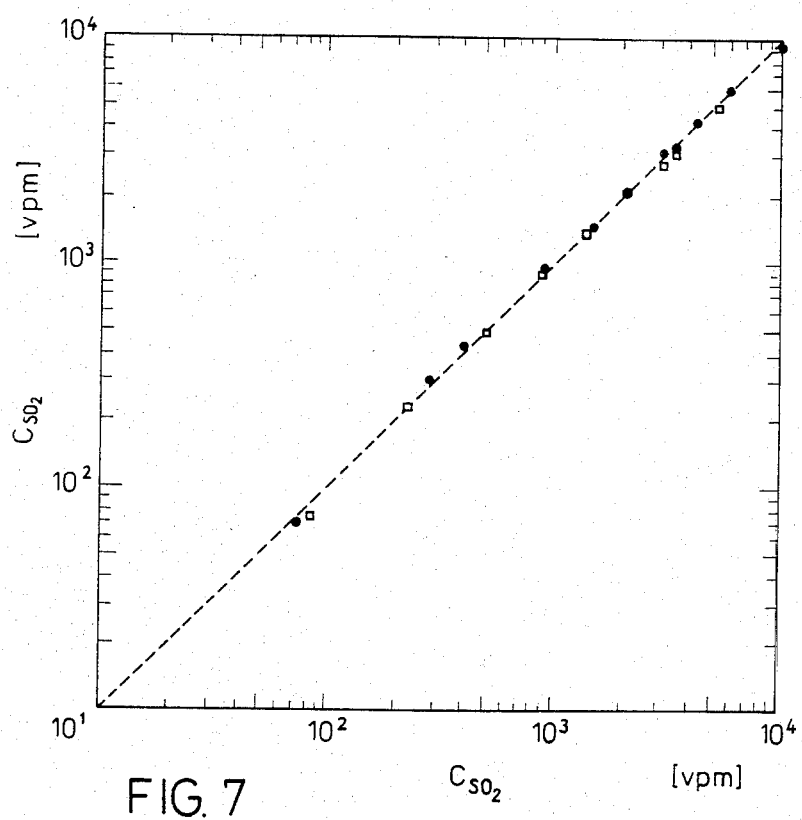
FIG. 7 shows a calibration curve.

The calibration curve shown in FIG. 7 is obtained from a cell of the present invention having a total internal volume of about 10 ml which electrolyte (0.5M sulfuric acid, 0.2M copper sulfate) is replaced at a replacement rate of between 10 and 20 ml. per minute at a temperature of 20° C. The calibration is carried out utilizing of mixture of sulphur dioxide as indicated in nitrogen carrier at a flow rate of 380 ml. of gas per minute. The signal level is substantially stable at constant $SO_2$ concentration. A 20% change in the signal height (for $\tau_{90}$) requires approximately 110 seconds when the exchange rate is less than $0.5\tau_{90}$ becomes substantially longer (200 seconds or more). The signal stability is then small and the steepness of the calibration curve is reduced.

We claim:

1. An apparatus for polarographic analysis of sulphur dioxide in gases by measurement of the anodic oxidation current due to said sulphur dioxide comprising:
   (a) a housing having a first and a second tubular chamber and upper and lower connecting means for interconnecting said chambers at their upper and lower portions respectively,
   said second chamber being formed by a substantially vertical shaft in a log or block and said first chamber being formed by an other shaft oriented at an acute angle to the axis of said second chamber,
   (b) a measuring electrode witin said second chamber,
   (c) a non-polarizable counter-electrode within said second chamber spaced apart from said measuring electrode so as to permit electrolyte to be placed therebetween;
   a gas inlet tube having an entrance and, within said first chamber, having an opening proximate to the bottom part of said chamber for the introduction of gas to be analyzed into said chamber when said housing is filled with electrolyte, the difference of the density of the electrolyte containing gas bubbles in said first chamber and the no-gas-bubbles containing electrolyte in the second one being capable of creating a circulation of gas saturated electrolyte in the housing when said housing is charged with electrolyte,
   (e) means for connecting a source of electrical potential across said electrodes,
   (f) means for measuring the current flowing between said electrodes when the device is charged with electrolyte, gas passed thereinto and potential applied across the electrodes,
   (g) inflow and outflow means for the continued supply of fresh electrolyte to said chamber,
   the inflow means for the fresh electrolyte being located to discharge into said upper connecting means, and
   comprises a constant level storage tank positioned above the said upper connecting means; and
   a capilliary tube journaled thru the base of said storage tank, the upper end thereof being below the liquid level in said container and the lower end thereof within said upper connecting means,
   (h) cartridge means charged with activated charcoal, said charcoal having grains of sufficient size to permit simultaneous wetting thereof by said electrolyte and penetration of air therebetween, comprising an inflow means, an outflow means and an air access means; said flow means being connected to the outflow means from said chambers,
   (i) electrolyte inflow control means, connected to the outflow means to said chambers, having inflow and outflow means, and
   (j) outer circulating means connected between the outflow means of said cartridge and the inflow means of said electrolyte control means for circulating electrolyte therebetween,
   the electrolyte inflow control means (i) being conceived for a constant electrolyte supply corresponding to an electrolyte exchange in the cell in the range of 0.5 to 5 of total cell volume per minute, and
   the cartridge size and arrangement of its inflow and outflow means being thus adapted to the electrolyte exchange per minute that the activated charcoal is at least partially merely wetted by the electrolyte passing the cartridge.

2. An apparatus for polarographic analysis of sulphur dioxide in gases by measurement of the anodic oxidation current due to said sulphur dioxide comprising:
   (a) a housing having a first and a second tubular chamber and upper and lower connecting means for interconnecting said chambers at their upper and lower portions respectively,
   (b) a measuring electrode within said second chamber,
   (c) a non-polarizable counter-electrode within said second chamber spaced apart from said measuring electrode so as to permit electrolyte to be placed therebetween;
   (d) a gas inlet tube having an entrance and, within said first chamber, having an opening proximate to the bottom part of said chamber for the introduction of gas to be analyzed into said chamber when said housing is filled with electrolyte, the difference of the density of the electrolyte containing gas bubbles in said first chamber and the no gas bubbles containing electrolyte in the second one being capable of creating a circulation of gas saturated electrolyte in the housing when said housing is charged with electrolyte,
   (e) means for connecting a source of electrical potential across said electrodes,
   (f) means for measuring the current flowing between said electrodes when the device is charged with electrolyte, gas passed thereinto and potential applied across the electrodes,
   (g) inflow and outflow means for the continued supply of fresh electrolyte to said chambers,
   (h) cartridge means charged with activated charcoal said charcoal having grains of sufficient size to permit simultaneous wetting thereof by said electrolyte and penetration of air therebetween, comprising an inflow means, an outflow means and an air access means; said flow means being connected to the outflow means from said chambers,
   (i) electrolyte inflow control means, connected to the outflow means to said chambers, having inflow and outflow means, and
   (j) outer circulating means connected between
      (i) the outflow means of said cartridge comprising a storage vessel, a water source connected to said vessel, a level control means operative upon said water source, and a pump means, whereby said control, cooperating with said water source, maintains a constant electrolyte level in said storage vessel, and
      (ii) the inflow means of said electrolyte control means for circulating electrolyte therebetween,
   the electrolyte inflow control means (i) being conceived for a constant electrolyte supply corresponding to an electrolyte exchange in the cell in the range of 0.5 to 5 of total cell volume per minute, and
   the cartridge size and arrangement of its inflow and outflow means being thus adapted to the electrolyte exchange per minute that the activated charcoal is at least partially merely wetted by the electrolyte passing the cartridge.

3. An apparatus for polarographic analysis of sulphur dioxide in gases by measurement of the anodic oxidation current due to said sulphur dioxide comprising:
   (a) a housing having a first and a second tubular chamber and upper and lower connecting means for interconnecting said chambers at their upper and lower portions respectively,
   (b) a measuring electrode witin said second chamber,
   (c) a non-polarizable counter-electrode within said second chamber spaced apart from said measuring electrode so as to permit electrolyte to be placed therebetween;
   (d) a gas inlet tube having an entrance and, within said first chamber, having an opening proximate to the bottom part of said chamber for the introduction of gas to be analyzed into said chamber when said housing is filled with electrolyte, the difference of the density of the electrolyte containing gas bubbles in said first chamber and the no gas bubbles containing electrolyte in the second one being capable of creating a circulation of gas saturated electrolyte in the housing when said housing is charged with electrolyte,
   further comprising a gas pressure control means attached to the entrance end of the gas inlet tube, comprising a housing,
   a flexible corrosion resistant membrane with said housing dividing said housing into a first and a second chamber,
   an adjustable spring biasing means within said first chamber biasing said membrane towards said second chamber,
   an air access means witin said first chamber,
   a gas inflow and a gas outflow means penetrating into said second chamber,
   (e) means for connecting a source of electrical potential across said electrodes,
   (f) means for measuring the current flowing between said electrodes when the device is charged with electrolyte, gas passed thereinto and potential applied across the electrodes,
   (g) inflow and outflow means for the continued supply of fresh electrolyte to said chambers,
   (h) cartridge means charged with activated charcoal, said charcoal having grains of sufficient size to permit simultaneous wetting thereof by said electrolyte and penetration of air therebetween, comprising an inflow means, an outflow means and an air access means; said flow means being connected to the outflow means from said chambers,
   (i) electrolyte inflow control means, connected to the outflow means to said chambers, having inflow and outflow means, and
   (j) outer circulating means connected between the outflow means of said cartridge and the inflow means of said electrolyte control means for circulating electrolyte therebetween,
   the electrolyte inflow control means (i) being conceived for a constant electrolyte supply corresponding to an electrolyte exchange in the cell in the range of 0.5 to 5 of total cell volume per minute, and
   the cartridge size and arrangement of its inflow and outflow means being thus adapted to the electrolyte exchange per minute that the activated charcoal is at least partially merely wetted by the electrolyte passing the cartridge.

* * * * *